(12) United States Patent
Frost et al.

(10) Patent No.: US 11,065,390 B2
(45) Date of Patent: Jul. 20, 2021

(54) AUTOMATIC DELIVERY DEVICE WITH END OF INJECTION INDICATION DEVICE

(71) Applicant: Carebay Europe Ltd., Sliema (MT)

(72) Inventors: Jason Frost, Boca Raton, FL (US); Mattias Daniel, Täby (SE); Sebastian Karlsson, Stigtomta (SE)

(73) Assignee: SHL MEDICAL AG, Zug (CH)

( * ) Notice: Subject to any disclaimer, the term of this patent is extended or adjusted under 35 U.S.C. 154(b) by 245 days.

(21) Appl. No.: 16/080,338

(22) PCT Filed: Jan. 20, 2017

(86) PCT No.: PCT/EP2017/051235
§ 371 (c)(1),
(2) Date: Aug. 28, 2018

(87) PCT Pub. No.: WO2017/148618
PCT Pub. Date: Sep. 8, 2017

(65) Prior Publication Data
US 2019/0022327 A1    Jan. 24, 2019

Related U.S. Application Data

(63) Continuation of application No. 15/056,614, filed on Feb. 29, 2016, now abandoned.

(51) Int. Cl.
*A61M 5/315* (2006.01)
*A61M 5/20* (2006.01)
(Continued)

(52) U.S. Cl.
CPC ........ *A61M 5/3157* (2013.01); *A61M 5/2033* (2013.01); *A61M 5/31528* (2013.01);
(Continued)

(58) Field of Classification Search
CPC ...... A61M 2205/583; A61M 2205/584; A61M 2205/582; A61M 2205/581;
(Continued)

(56) References Cited

U.S. PATENT DOCUMENTS 9,713,677 B2    7/2017  Daniel
2005/0027255 A1*  2/2005  Lavi ................... A61M 5/2033
                                                                604/135
(Continued)

FOREIGN PATENT DOCUMENTS

CH            705992 A2    6/2013
CN         103945879 A    7/2014
(Continued)

OTHER PUBLICATIONS

English Translation of Abstract of Japanese Patent Application No. 2015-520643 dated Oct. 17, 2019.
(Continued)

*Primary Examiner* — Brandy S Lee
*Assistant Examiner* — Hong-Van N Trinh
(74) *Attorney, Agent, or Firm* — Mcdonnell Boehnen Hulbert & Berghoff LLP

(57) ABSTRACT

A drive mechanism for a delivery device comprising a rotator comprising an outer surface and an inner surface, the rotator configured to rotate from a first position to a second position; and a needle cover comprising an inner surface that engages the outer surface of the rotator. An end of injection indication device is positioned at least partially within a plunger rod spring, the end of injection indication device providing a signal to a user of the drive mechanism that an injection has been completed.

23 Claims, 20 Drawing Sheets

(51) Int. Cl.
*A61M 5/32* (2006.01)
*G16H 20/17* (2018.01)

(52) U.S. Cl.
CPC ...... *A61M 5/31551* (2013.01); *A61M 5/3204* (2013.01); *G16H 20/17* (2018.01); *A61M 2005/2013* (2013.01); *A61M 2205/3386* (2013.01); *A61M 2205/581* (2013.01); *A61M 2205/582* (2013.01); *A61M 2205/584* (2013.01)

(58) Field of Classification Search
CPC .. A61M 5/3157; A61M 5/31551; A61M 5/20; A61M 5/31528; A61M 5/2033; A61M 2005/2013; A61M 5/3202; A61M 5/326; A61M 5/24; A61M 5/31585; A61M 5/31501; A61M 2005/206; A61M 2005/3267; A61M 5/3243; A61M 5/31511; A61M 5/3158; A61M 2205/58; A61M 2205/585; A61M 2205/586; A61M 2205/587; A61M 5/3204; A61M 2205/3386; A61M 2005/208; A61M 2005/3247; A61M 5/315; A61M 5/32; A61M 5/31
See application file for complete search history.

(56) References Cited

U.S. PATENT DOCUMENTS

| | | |
|---|---|---|
| 2013/0041347 A1* | 2/2013 | Daniel ................. H05K 999/99 604/506 |
| 2013/0317434 A1 | 11/2013 | Fabien et al. |
| 2015/0165129 A1 | 6/2015 | Row et al. |
| 2016/0008542 A1* | 1/2016 | Hirschel ................. A61M 5/24 604/137 |

FOREIGN PATENT DOCUMENTS

| CN | 105246528 A | 1/2016 |
|---|---|---|
| JP | 2013-526904 A | 6/2013 |
| JP | 2015-520643 A | 7/2015 |
| WO | 2011123024 A1 | 10/2011 |
| WO | 2013034651 A1 | 3/2013 |
| WO | 2015/004048 A1 | 1/2015 |

OTHER PUBLICATIONS

English Translation of Abstract of Swiss Patent No. 705,992 dated Aug. 8, 2018.
Chinese Office Action for CN Application No. 201780011141.5, dated Apr. 26, 2020.

* cited by examiner

AUTOMATIC DELIVERY DEVICE WITH END OF INJECTION INDICATION DEVICE

CROSS REFERENCE TO RELATED APPLICATIONS

The present application is a U.S. National Phase Application pursuant to 35 U.S.C. § 371 of International Application No. PCT/EP2017/051235 filed Jan. 20, 2017, which claims priority to U.S. patent application Ser. No. 15/056,614 filed Feb. 29, 2016. The entire disclosure contents of these applications are hereby incorporated by reference into the present application.

FIELD

The present disclosure relates to a delivery device and in particular to an improved, user-friendly, medicament delivery device providing an audible, tactile and/or visual signal or confirmation to a user when an injection has been made.

BACKGROUND

Medicament delivery devices are developed for self-administration, i.e. a user performs the medicament delivery her-, or himself. This requires a medicament delivery device that is safe to use and easy to handle. In order to meet these requirements, the risk of human errors should be minimized, the number of actions needed to be performed in order to receive a dose need to be reduced, and the device should be intuitive and ergonomic to use.

Accordingly, there is a need for cost effective methods and delivery devices that minimize the risk of human errors and it is desirable to have the delivery device that reduces the number of actions needed to be performed in order to receive a dose. There is also a need for a delivery device that provides a confirmation that a delivery device injection has been completed.

SUMMARY

According to an exemplary embodiment, a drive mechanism for a delivery device is disclosed. The drive mechanism comprises a rotator comprising an outer surface and an inner surface, the rotator configured to rotate from a first position to a second position and a needle cover comprising an inner surface that engages the outer surface of the rotator. The drive mechanism further comprises a plunger rod spring positioned within a cavity defined by the rotator. An end of injection indication device is positioned at least partially within the plunger rod spring, the end of injection indication device providing a signal to a user of the drive mechanism that an injection has been completed.

These as well as other advantages of various aspects of the present patent application will become apparent to those of ordinary skill in the art by reading the following detailed description, with appropriate reference to the accompanying drawings.

BRIEF DESCRIPTION OF THE DRAWINGS

The novel features believed characteristic of the illustrative embodiments are set forth in the appended claims. The illustrative embodiments, however, as well as a preferred mode of use, further structures and descriptions thereof, will best be understood by reference to the following detailed description of an illustrative embodiment of the present disclosure when read in conjunction with the accompanying drawings, wherein:

DETAILED DESCRIPTION

In the present application, when the term "proximal part/end" is used, this refers to the part/end of the delivery device, or the parts/ends of the members thereof, which is/are located the furthest away from the medicament delivery site of the patient. Correspondingly, when the term "distal part/end" is used, this refers to the part/end of the delivery device, or the parts/ends of the members thereof, which, is/are located closest to the medicament delivery site of the patient.

Figure 1:
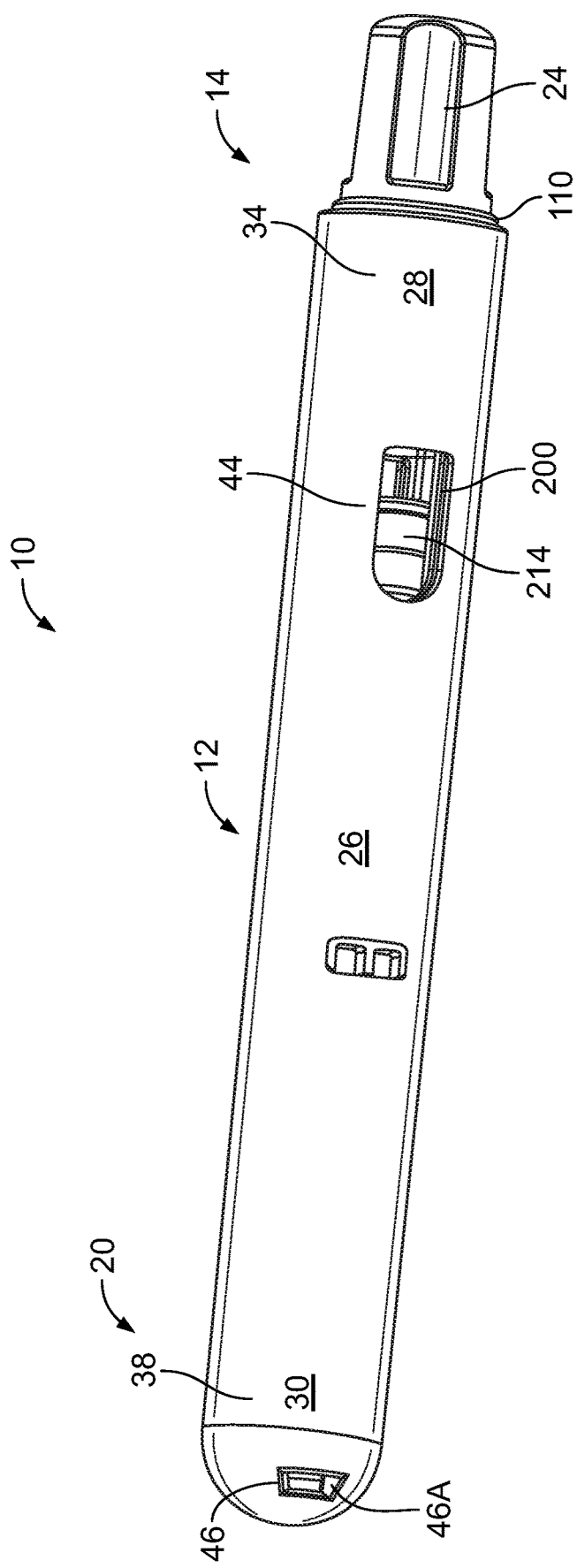
FIG. 1 is a diagrammatic representation of a delivery device.

FIG. 1 is a diagrammatic representation of a delivery device 10, such as a medical delivery device for delivering a set dose of a medicament contained within a container of the delivery device 10. The delivery device 10 comprises a distal end 14 and a proximal end 20. FIG. 1 illustrates, in perspective, an outer shell 26 of an exemplary medicament delivery device 10 wherein the outer shell 26 houses a drive mechanism 12 for administering a dose of a medicament contained within a container housed within the outer shell 26. As illustrated, the delivery device 10 resides in an initial, non-activated, state of the medicament delivery device 10 having a cap 24 provided near the distal end 14 of the delivery device 10. The cap 24 comprises a proximal end surface, abutting with the distal end surface of the annular contact member 31 of the needle cover 110 such that when the cap 24 is manually operated and detached, it allows the needle cover 110 to be moved by the force from a needle cover spring 50 (FIG. 2) from a non-activated position to an activated position, away from the distal end 14 of the delivery device 10.

As illustrated, the outer shell 26 comprises a generally tubular shape that extends from an outer shell distal end 28 and an opposite, proximal end 30. The outer shell 26 further comprises a first viewing opening or window 44 and a second viewing opening or window 46. The first viewing opening 44 is provided near the distal end 34 of the outer shell 26. This first viewing opening 44 allows a user to determine the position of a stopper 214 of a container 200 that is fixedly contained within the delivery device 10. As such, the first viewing opening 44 allows a user to determine whether the delivery device 10 has already been activated to deliver a dose.

The second viewing opening or window 46 of the outer shell 30 is provided near a proximal end 30 of the outer shell 26. The proximal end 30 of the outer shell 26 may comprise two second viewing openings 46 A, B. (FIG. 1 only illustrates one second viewing opening 46 A). As will be described in greater detail herein, the second viewing opening 46 provides a user of the delivery device 10 the ability to view an end of injection indication mechanism after an injection has been completed.

Figure 2:
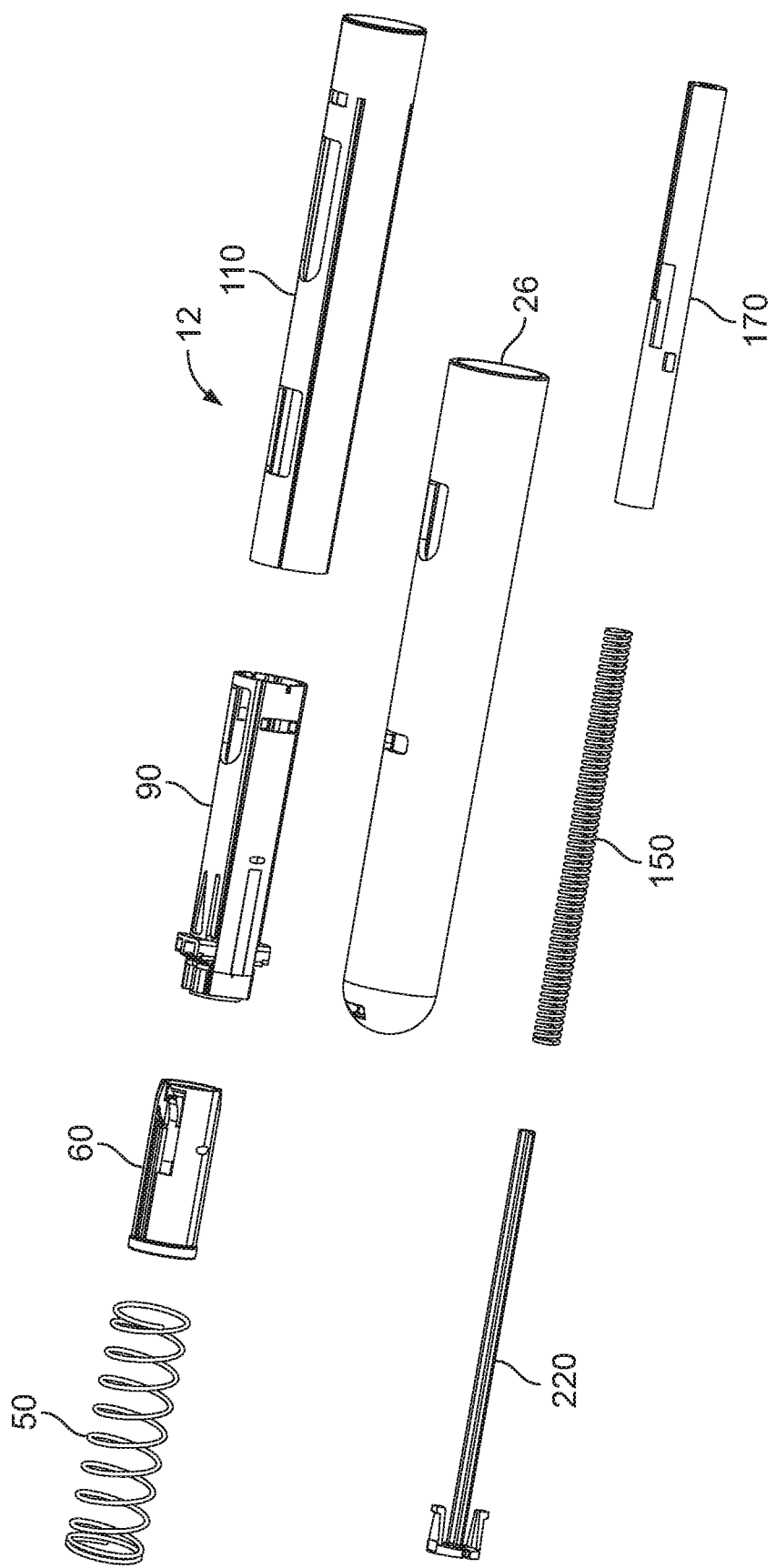
FIG. 2 is a diagrammatic representation of various component parts making up a drive mechanism of the delivery device illustrated in FIG. 1.

FIG. 2 illustrates various component parts of the drive mechanism 12 for use with the delivery device 10 illustrated in FIG. 1. Specifically, these component parts include: an outer shell 26; a needle cover spring 50; a rotator 60; a cartridge housing 90; a needle cover 110; a guide rod 220; a plunger rod spring 150; and a plunger rod 170.

Figure 3A:
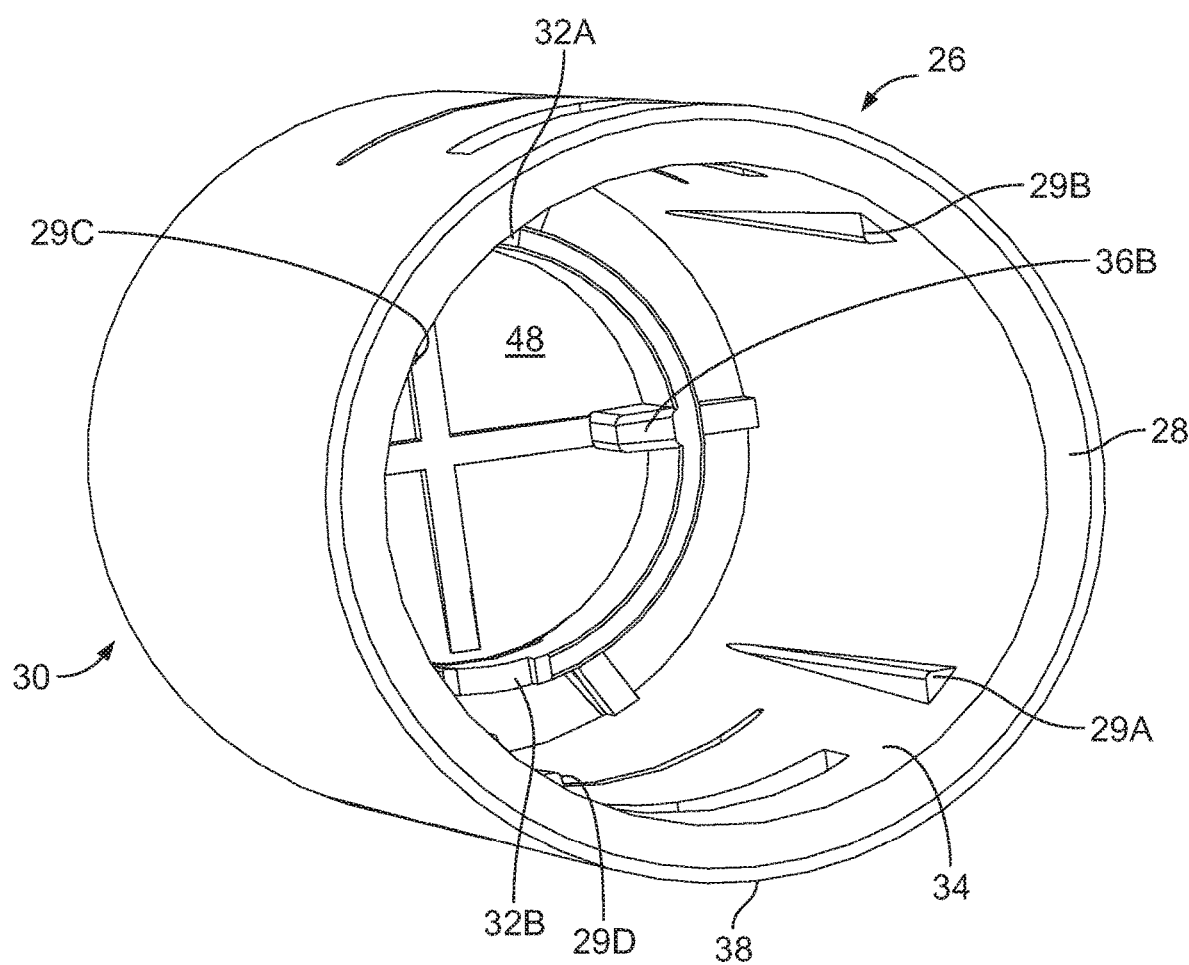
FIG. 3A is a diagrammatic representation of the outer shell illustrated in FIG. 2.
Figure 3B:
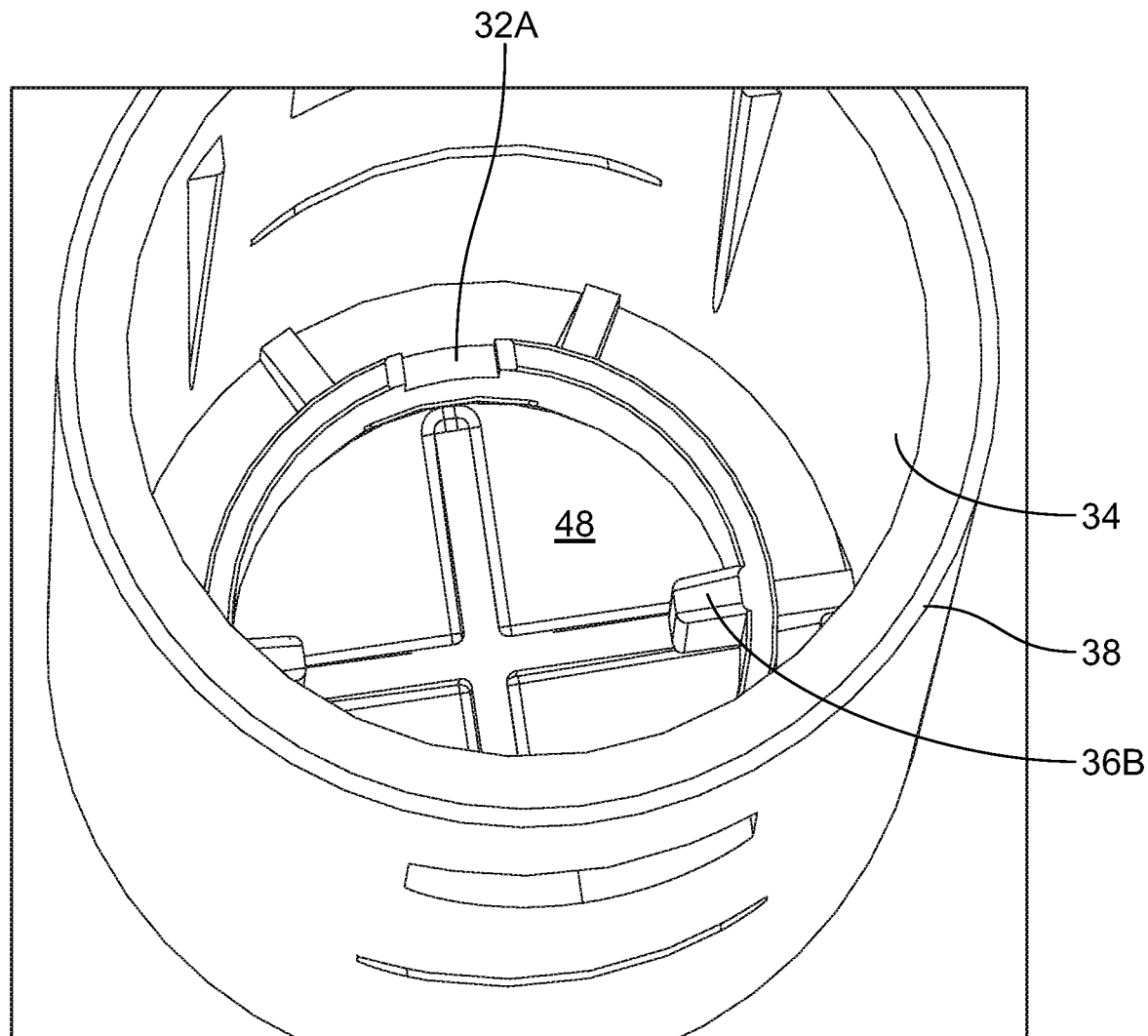
FIG. 3B is another diagrammatic representation of the outer shell illustrated in FIG. 3A.
Figure 4:
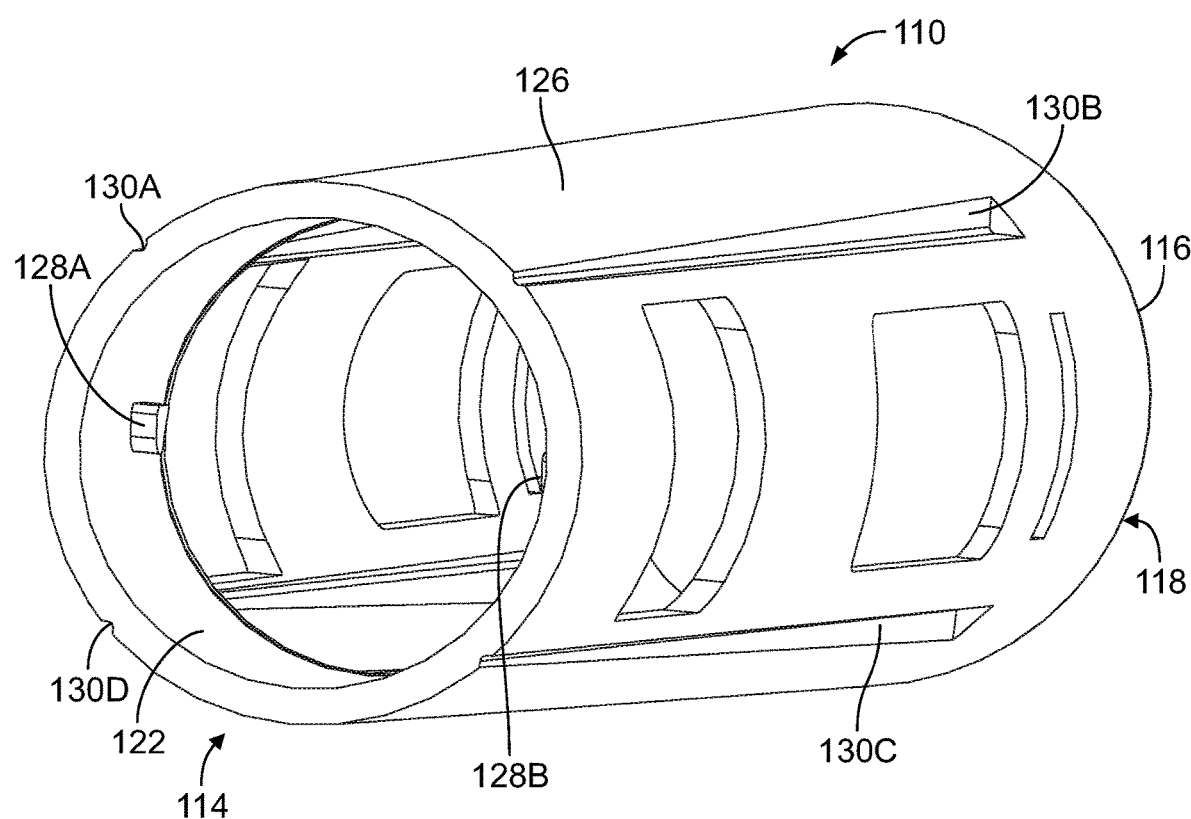
FIG. 4 is a diagrammatic representation of the needle shield illustrated in FIG. 2.

FIG. 3A is a diagrammatic representation of the outer shell 26 illustrated in FIG. 2 and FIG. 3B is another diagrammatic representation of the outer shell 26 illustrated in FIG. 3A. As illustrated, the outer shell 26 comprises a generally tubular shape that extends from a distal end 28 to a proximal end 30. The outer shell 26 further comprises both an inner surface 34 and an outer surface 38. The inner surface 34 comprises a plurality of longitudinal protrusions 29 A,B,C,D that are configured to engage a plurality of grooves 130 A,B,C,D that are provided along an outer surface 126 of the needle cover 40 (FIG. 4). In this preferred arrangement, the plurality longitudinal protrusions 29 A,B,C,D comprise a varying width.

In addition, and as illustrated in FIGS. 3A and 3B, the outer shell 26 further comprises a proximal end wall 48 and this proximal end wall 48 comprises a number of retaining structures 32 and guiding structures 36. Specifically, the proximal end wall 48 comprises two retaining structures 32 A, B. As will be described in greater detail herein, the retaining structures 32 A, B retain the guide rod 220 in a non-activated position prior to an injection event. In addition, the proximal end wall 48 further comprises a plurality of guiding features 36. As will be described in greater detail herein, these guiding features 36 are configured to help guide the guide rod 220 during an injection event (e.g., when the guide rod 220 moves in a proximal direction).

FIG. 4 illustrates the needle cover 110 of the delivery device 10 illustrated in FIGS. 1 and 2. As illustrated, the needle cover 110 comprises a generally tubular shape that extends from a proximal end 114 to a distal end 118. An annular contact member 116 is provided at the distal end 114 of the needle cover 110. This annular contact member 116 is used by a user of the delivery device 10 to place this annular contact member 116 at an injection site so as to initiate an injection of the delivery device 10.

The needle cover 110 further comprises an outer surface 126 that extends from the proximal end 114 to the distal end 118. The needle cover 110 further comprises an inner surface 122 that extends from the proximal end 114 to the distal end 118. Located near the proximal end 114 of the needle cover 110, along the inner surface 122, a radially, inwardly directed pin 128A is provided. In this illustrated arrangement, at least one pin 128 A is provided along this inner surface 122. Preferably, the needle cover 110 comprises two pins 128 A, B that are offset by 180 degrees from one another along the inner surface of the needle cover 110. As will be described in greater detail herein, the pins 128 A, B of the needle cover 110 are used to interact with a groove configuration 70 that is provided by an outer surface 64 of the rotator 60, so that an injection function can be achieved.

The needle cover 110 further comprises a plurality of guide grooves 130 A,B,C,D provided along the outer surface 126 of the needle cover 110. As illustrated, these guide grooves 130 A-Dare equally spaced around the outer circumference of the needle cover 110. In this preferred arrangement, these guide grooves 130 A-D start at the proximal end 114 of the needle cover 110 and extend in a linear manner towards the distal end 118 of the needle cover 110. In this illustrated arrangement, each of the guide grooves 130 A-D comprise a varying width groove. Specifically, the width of the guide grooves 130 A-D increases as each of the grooves extend towards the distal end 118 of the needle cover 110. These guide grooves 130 A-D are configured to interact with the plurality of outer shell protrusions 29 A-D (see, e.g., FIG. 3A) so as to rotationally fix the needle cover 110 to the outer shell 26.

Figure 5A:
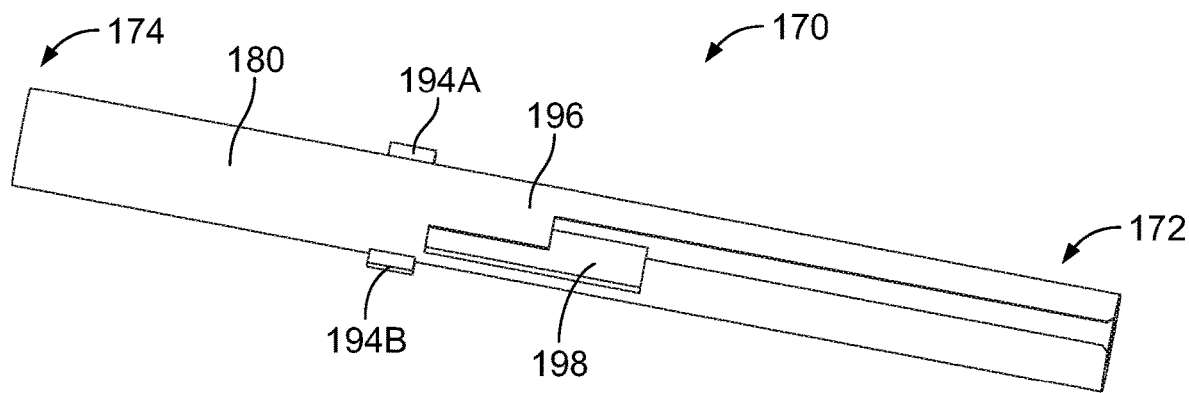
FIG. 5A is a diagrammatic representation of the plunger rod illustrated in FIG. 2.
Figure 5B:
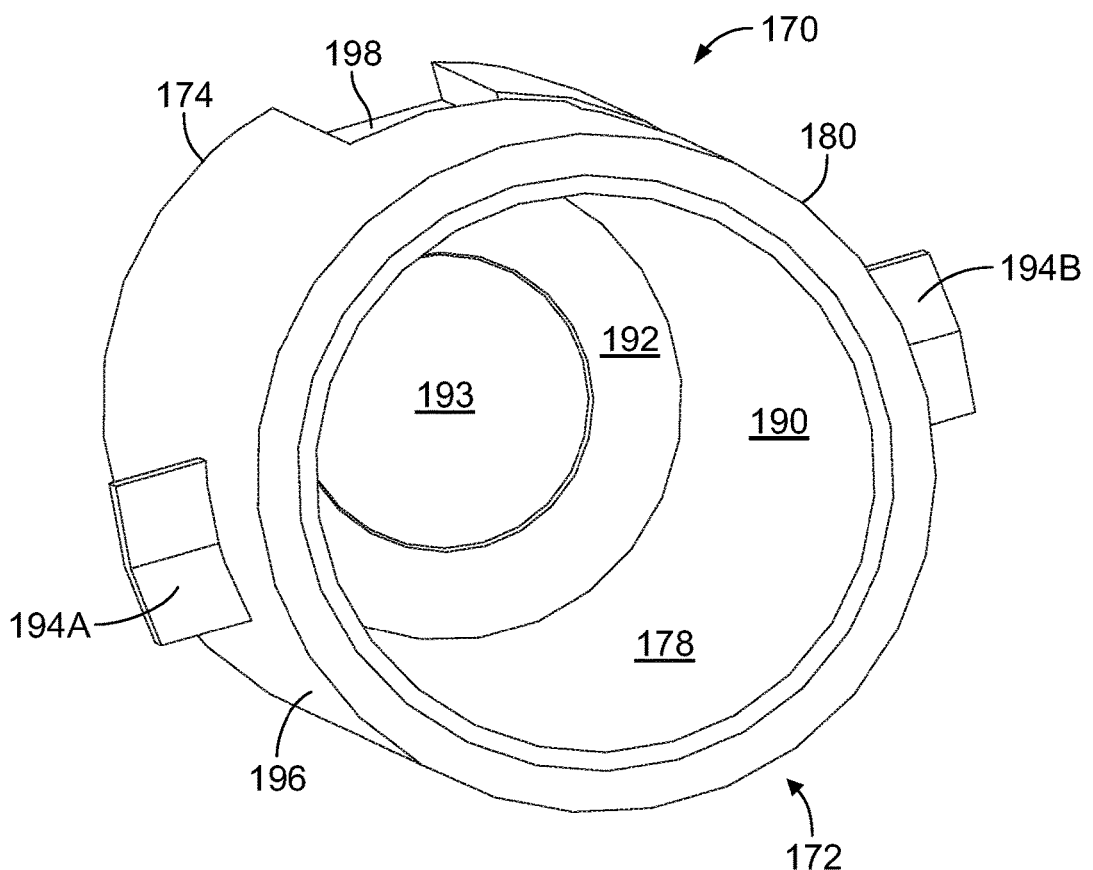
FIG. 5B is another diagrammatic representation of the plunger rod illustrated in FIG. 5A.

FIG. 5A illustrates is a diagrammatic representation of the plunger rod 170 illustrated in FIG. 2 and FIG. 5B illustrates another diagrammatic representation of the plunger rod 170 illustrated in FIG. 2. As illustrated, the plunger rod 170 comprises a distal end 172 and a proximal end 174. The plunger rod 170 further comprises an outer surface 180 that extends from the distal end 172 towards the proximal end 174. Similarly, and as can be seen from FIG. 5B, the plunger rod 170 further comprises in inner surface 178 that extends from the distal end 172 towards the proximal end 174. As such, in this illustrated arrangement, the plunger rod 170 comprises a hollow plunger rod defining an inner cavity 190. Preferably, this inner cavity 190 extends from a plunger rod distal end wall 192 towards the proximal end 174 of the plunger rod 170. As will be explained in detail herein, the inner cavity 190 of the plunger rod 170 is configured to contain both the plunger rod spring 150 and the guide rod 220. Specifically, the plunger rod 170 may be configured such that the inner cavity 190 of the plunger rod 170 houses the guide rod 220 positioned within an internal cavity defined by the plunger rod spring 150. In such a preferred arrangement, the distal end wall 192 defines an opening 193 that allows the guide rod 220 to pass through the plunger rod 170.

As illustrated, the outer surface 180 of the plunger rod 170 comprises a generally smooth outer surface 196. In this illustrated arrangement, the outer surface 180 of the plunger rod 170 comprises at least one rib 194 A. In this plunger rod arrangement, the outer surface 180 is configured with two ribs 194 A, B. As illustrated, each rib 194 A, B is configured as a rib comprising a generally rectangular form, however, alternative rib geometrical configurations may also be used. Each rib 194 A, B is configured to extend generally vertically away from the outer surface 180 of the plunger rod 170. As will be described in greater detail herein, with the delivery device 10 as illustrated in FIG. 1, the plunger rod ribs 194 A, B are configured to interact with corresponding ribs 80 provided along an inner surface 68 of the rotator 60 (FIGS. 6A and 6B).

Aside from the ribs 196 A, B, the plunger rod outer surface 180 further comprises a plunger rod retaining part 198. As illustrated, this plunger rod retaining part 198 comprises a cut out or recess that extends along at least a portion of the plunger rod outer surface 180 near the distal end 172 of the plunger rod 170.

Figure 6A:
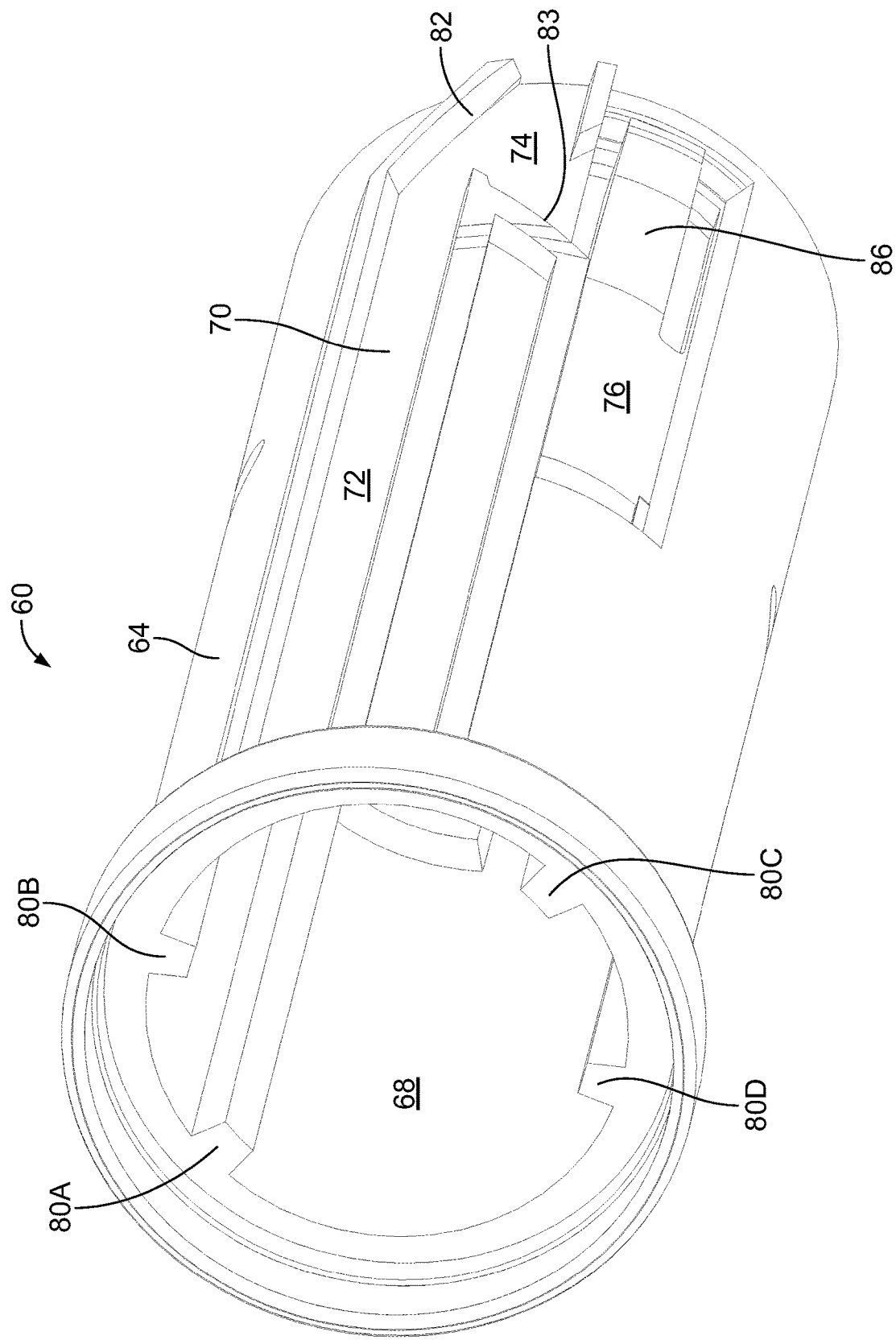
FIG. 6A is a diagrammatic representation of the rotator illustrated in FIG. 2.
Figure 6B:
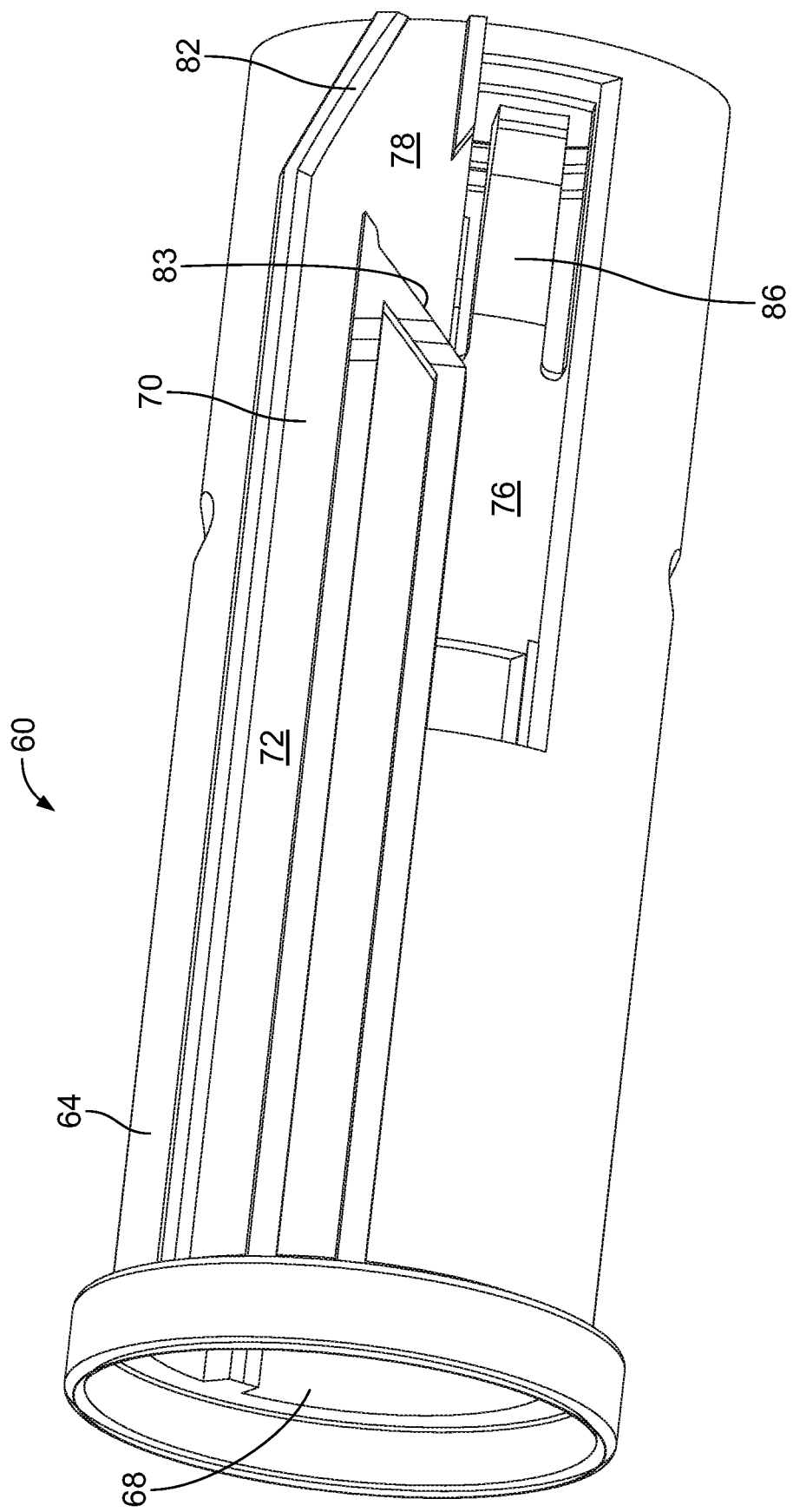
FIG. 6B is another diagrammatic representation of the rotator illustrated in FIG. 6A.

FIG. 6A is a diagrammatic representation of the rotator 60 illustrated in FIG. 2 and FIG. 6B is another diagrammatic representation of rotator 60 illustrated in FIG. 2. Referring to FIGS. 6A and 6B, the rotator 60 comprises a generally cylindrical shape comprising both an outer surface 64 and an inner surface 68. The outer surface 64 is configured with a track configuration 70, comprising one or more track portions. In one preferred arrangement, the track configuration 70 comprises a first track portion 72, a second track portion 74, and a third track portion 76. As will be described in greater detail herein, the various track portions 72, 74, 76 within the track configuration 70 are structured to cooperate with the needle cover pins 128 A, B provided along the inner surface 122 of the needle cover 110, such that longitudinal movement of the needle cover 110 in the distal/proximal directions rotates the rotator 60 in a predetermined direction.

In addition, the rotator 60 further comprises at least one rib 80 that is provided along the rotator inner surface 68 residing within a cavity 69 defined by the rotator 60. For example, in this illustrated arrangement, the rotator 60 comprises four ribs 80 A, B, C, D that extend radially inward within this cavity 69, and away from the inner surface 68 of the rotator 60. As will be described in greater detail herein, during an injection step when the rotator 60 is rotated by interaction with longitudinal movement of the needle cover pins 128 A, B, the rotator ribs 80 A-D are configured to engage and act upon the radially extending ribs 194 A, B of the plunger rod 170, so as to rotate the plunger rod 170. Rotation of the plunger rod 170 acts to release the plunger rod 170 from the cartridge housing. As such, once the plunger rod 170 is released from the cartridge housing and since it remains under the force of a compressed plunger rod spring 150, the plunger rod 170 is driven in a distal direction so as to inject a dose of medication from a container contained within the delivery device 10.

Figure 7A:
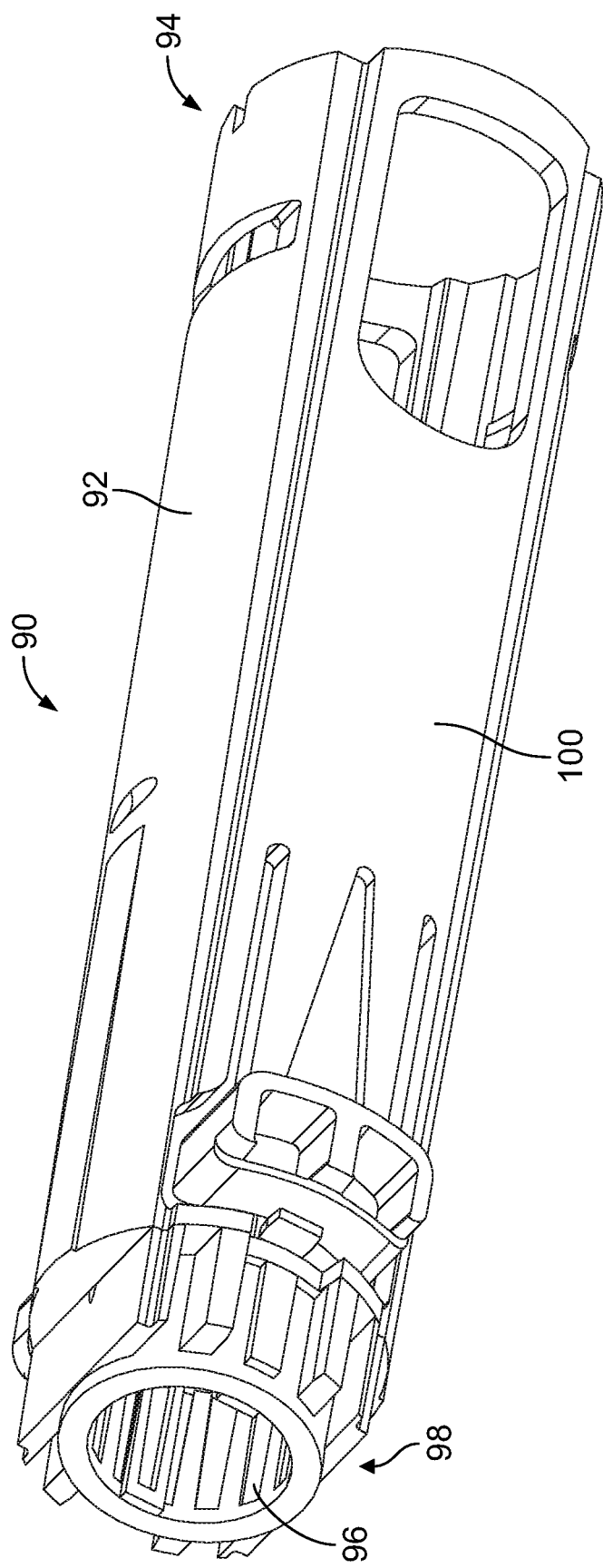
FIG. 7A is a diagrammatic representation of the cartridge housing illustrated in FIG. 2.
Figure 7B:
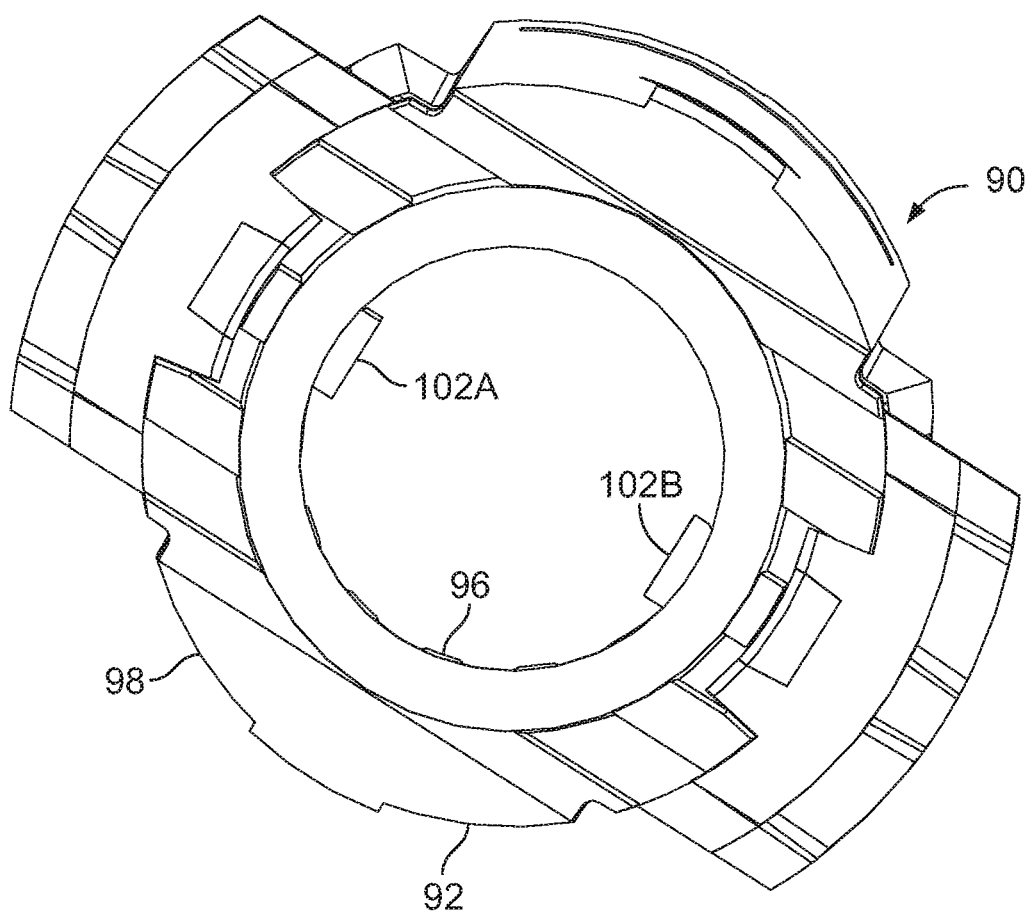
FIG. 7B is another diagrammatic representation of the cartridge housing illustrated in FIG. 7A.

FIG. 7A is a diagrammatic representation of the cartridge housing 90 illustrated in FIG. 2 and FIG. 7B is another diagrammatic representation of the cartridge housing 90 illustrated in FIG. 7A. Preferably, the cartridge housing 90 is fixedly attached to the outer shell 26. As illustrated, the cartridge housing 90 comprises an outside surface 100 having a generally cylindrical body 92 that extends from a distal end 94 to a proximal end 98 of the cartridge housing 90. In one arrangement, a plurality of cartridge housing ribs 102 A, B are provided along an inner surface 96 of the cartridge housing 90. As will be described in greater detail herein, the cartridge housing ribs 102 A, B are configured to engage the plunger rod retention part 198 when the delivery device 10 resides in a non-activated state. Once the delivery device 10 is activated, as the ribs of the rotator 60 engage the plunger rod ribs 194 A, B, the plunger rod 170 rotates. Plunger rod rotation releases the plunger rod retention part 198 from the cartridge housing ribs 102 A, B to thereby disengage the cartridge housing ribs 102 A, B from the plunger rod retention part 198.

As illustrated in FIG. 2, the drive mechanism further comprises a plunger rod spring 150. The plunger rod spring 150 preferably comprises a compression spring and is configured to reside within the inner cavity 180 defined by the plunger rod 170. Specifically, the plunger rod spring 150 is configured to act on the distal end wall 192 of the plunger rod 170 (FIG. SB) while being positioned circumferentially around the guide rod 220 as the drive mechanism 12 of the delivery device 10 resides in a non-activated state. Once the drive mechanism 12 is activated so as to release the plunger rod 170 in order to administer a dose of medicament contained with the container 200 within the cartridge housing 90, the plunger rod 170 is released from its fixed position, the plunger rod spring 150 acts upon the plunger rod 170 (i.e., specifically, the plunger rod spring 150 acts on the distal end wall 192 of the plunger rod 170) so as to drive the plunger rod 170 in the distal direction. This causes the distal end 172 of the plunger rod 170 to act upon the stopper 214 contained with the container 200 (FIG. 1) and to thereby inject the desired dose of medicament contained from the container 200.

Figure 8:
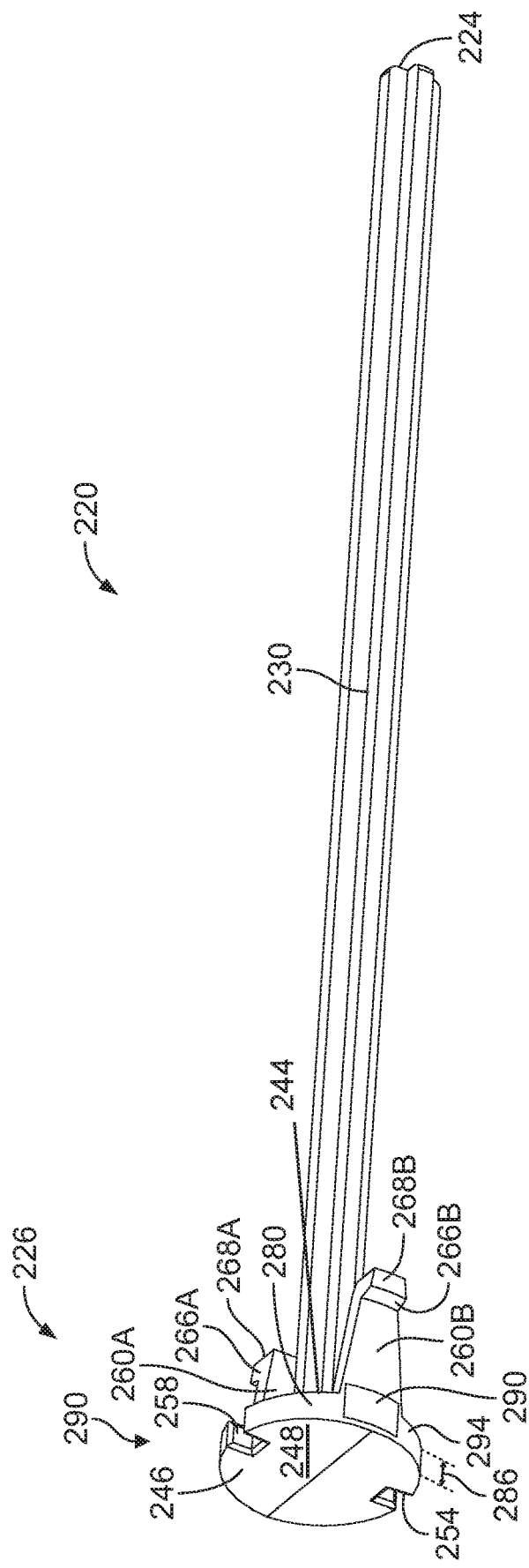
FIG. 8 is a diagrammatic representation of the guide rod illustrated in FIG. 2.

FIG. 8 is a diagrammatic representation of the guide rod 220 illustrated in FIG. 2. As illustrated, the guide rod 220 extends from a distal end 224 towards a proximal end 226. The guide rod 220 comprises an elongated member 230 that extends from the distal end 224 towards a disk shaped member 240 located near the proximal end 226 of the guide rod 220. This disk shaped member 240 comprises a distal surface 244 and a proximal surface 246. In this illustrated arrangement, the proximal surface 246 comprises a flat bearing surface 248 that is configured for acting or impinging upon the proximal end wall 48 of the outer shell 26 (FIGS. 3A and 3B) upon a completion of an injection step.

The guide rod 220 further comprises a plurality of flexible arms 260. Preferably, guide rod 220 comprises at least two flexible arms 260 A, B that are flexibly biased inwards, towards one another. Preferably, these two flexible arms 260 A, B are positioned 180 degrees apart from one another and extend away from the distal surface 244 of the disk shaped bearing member 240 towards the distal end 224 of the guide rod 220. In this illustrated arrangement, each flexible arm 260 A, B comprises a radially, outwardly directed hook 266. For example, the first flexible arm 260 A comprises a first radially, outwardly directed hook 266 A and the second flexible arm 260 B comprises a second radially, outwardly directed hook 266 B.

Preferably, each radially outwardly directed hook 266 A, B further comprises a chamfered edge. For example, the first radially outwardly directed hook 266 A comprises a first chamfered edge 268 A and the second radially outwardly directed hook 266 B comprises a second chamfered edge 268 B. As will be described in greater detail herein, the chamfered edges of the outwardly directed hooks 266 A, B allow the hooks to initially engage the outer shell retaining structures 32 (FIGS. 3A and 3B). The chamfered edges allow the hooks to be released from these retaining structures 32 after the plunger rod 170 has moved in the distal direction to administer the dose of medicament.

Preferably, the disk shaped bearing 240 also defines at least one slot for engaging the guiding structures 36 of the outer shell 26. In this preferred guide rod arrangement 220, the disk shaped member 240 defines two slots 254, 258 for engaging the two guiding structures 36 A, 8 provided by the proximal end wall 48 of the outer shell 30. In one preferred arrangement, during an injection step, the engagement of the slots 254, 258 with the guiding structures 36 A, 8 help to direct the guide rod 220 in the proximal direction. Specifically, in one preferred arrangement, the engagement of the slots 254, 258 with the guiding structures 36 A, 8 help to direct the guide rod 220 in the proximal direction so that a visual indication 290 may be properly viewed by way of a viewing window 44, 46.

In a preferred arrangement, disk shaped member 240 comprises a circumferential outwardly directed surface 280 comprising a defined width 286. Along at least a portion of this circumferential outwardly directed surface 280, a visual indicator 290 may be provided. In one preferred arrangement, this visual indicator 290 may comprise a first color that is different than a second color of the disk shaped member 240. In one arrangement, this visual indicator 290 may comprise text 294 that is viewable by a user of the delivery device 10 after an injection has been completed. As just one example, this text 294 may be inscribed along the outwardly directed surface 280 or may be provided by way of some type of label 298 that is affixed to this surface 280. Alternative visual indicating symbols and/or colors may also be used.

Figure 9:
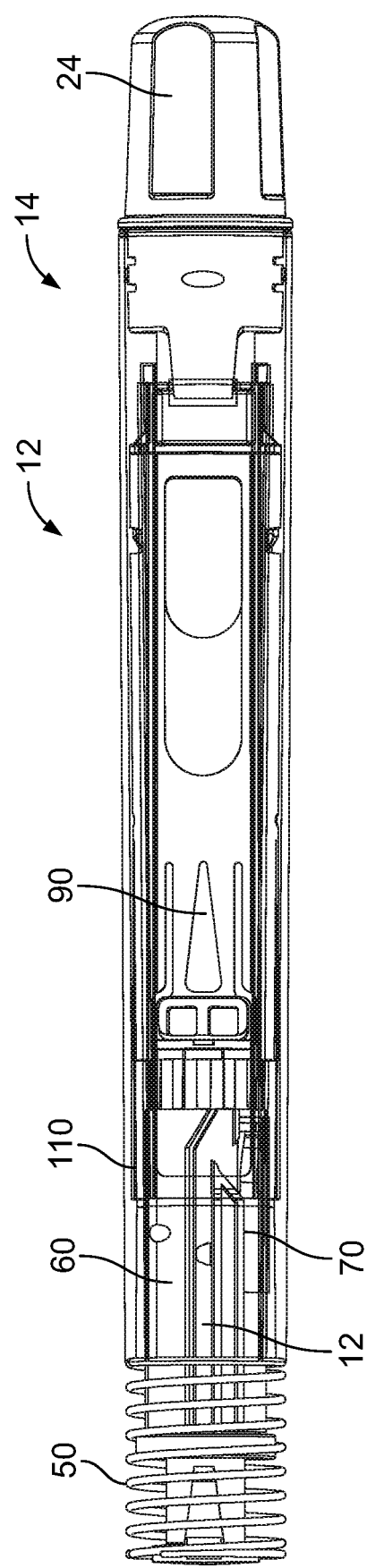
FIG. 9 is a diagrammatic representation of the drive mechanism of the delivery device illustrated in FIG. 1 with a cap attached.
Figure 10:
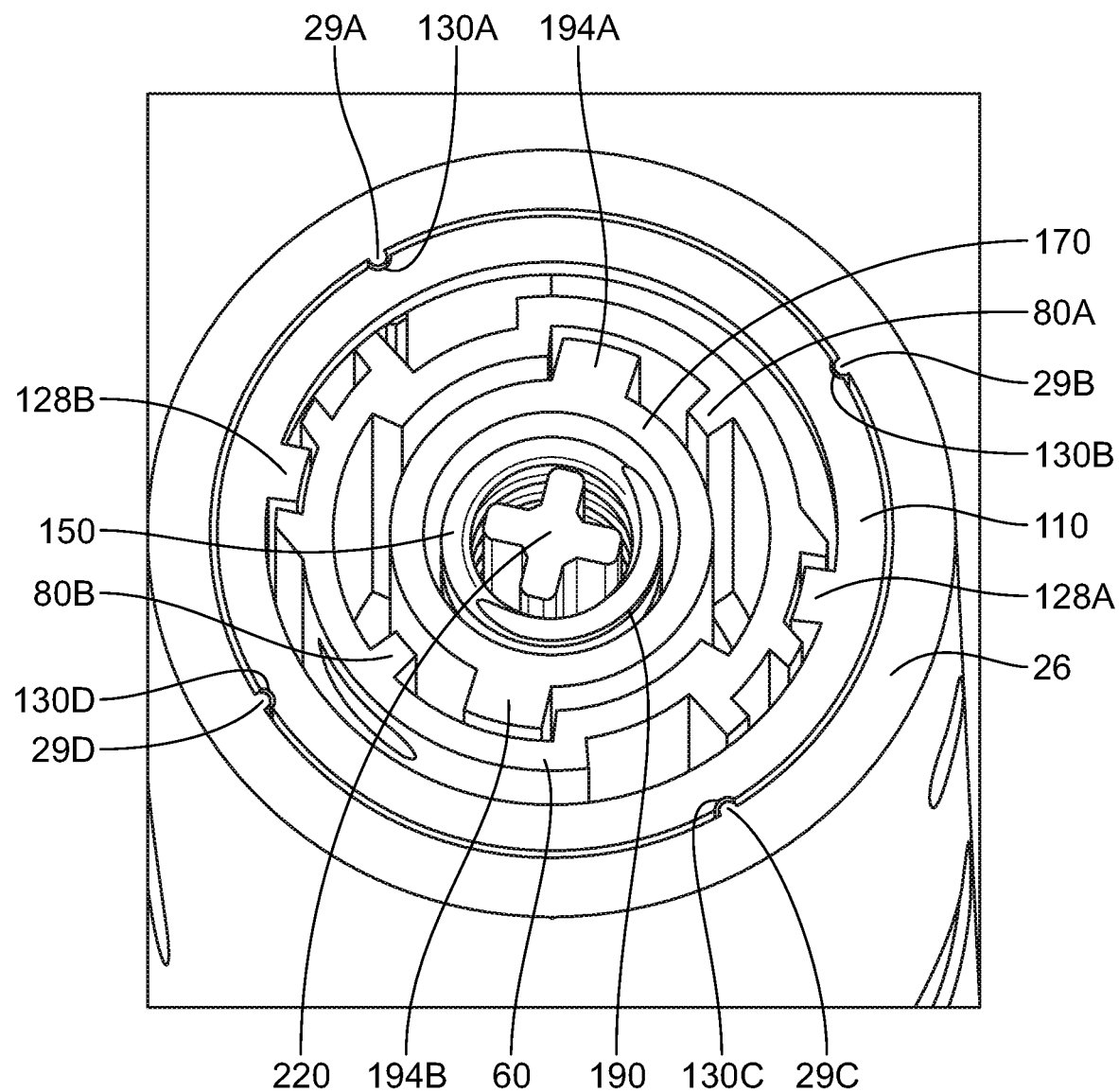
FIG. 10 is another diagrammatic representation of the drive mechanism illustrated in FIG. 9.

FIG. 9 illustrates various component parts of the drive mechanism 12 prior to removal of the cap 24 from the injection device 10. FIG. 10 illustrates various component parts of the drive mechanism 12 prior to removal of the cap 24 from the injection device 10 as illustrated in FIG. 9. Specifically, referring to FIGS. 9 and 10, the guide rod 220 of the drive mechanism 12 resides within the plunger rod spring 150 and this plunger rod spring 150 resides within the plunger rod cavity 190. The plunger rod 170 resides within the inner cavity 69 defined by the rotator 60. Importantly, the rotator inner ribs 80 A-D do not yet engage the outer ribs 194 A, B of the plunger rod 170. As also illustrated, the needle cover 110 is biased in the distal direction by way of the needle cover spring 50. In this biased position, the needle cover pins 128 of the needle cover 110 reside within the track portion 72 of the track configuration 70 defined by the outer surface 64 of the rotator 60. In this position, the grooves 130 A-D of the needle cover 110 remain engaged with the inner protrusions 29 A-D of the outer shell 26.

With reference to FIGS. 11 to 15, the operation of the drive mechanism 12 of the delivery device 10 will now be generally described. With reference to FIGS. 16A-17B, the operation of the delivery device 10 providing an audible, tactile and/or visual confirmation to a user when an injection has been made will be described.

Figure 11:
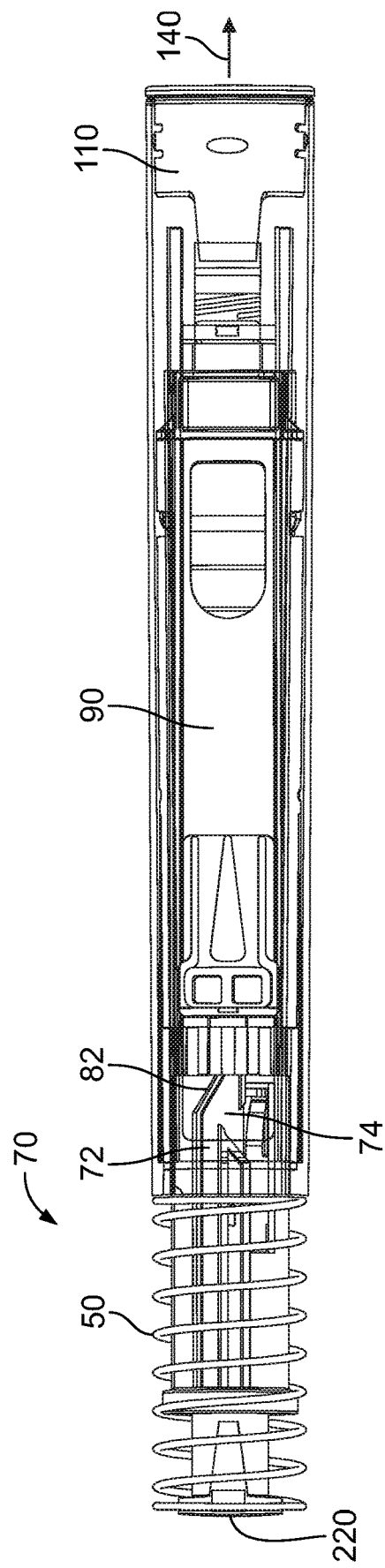
FIG. 11 is a diagrammatic representation of the drive mechanism illustrated in FIG. 9 with the cap removed.

For example, FIG. 11 illustrates the delivery device 10 with the outer shell 30 removed for ease of illustration and discussion. As can be seen from FIG. 11, with the cap 24 removed (see FIG. 9), the needle cover 110 is biased in the distal direction by way of the needle cover spring 50. The guide rod 220 is positioned within the plunger rod spring 150 and this plunger rod spring 150 is situated within the inner cavity defined by the plunger rod 170. In addition, the plunger rod spring 150 resides in a compressed state while providing a force that acts on the distal end wall 192 defined by the plunger rod 170. The plunger rod 170 is positioned within the rotator 60 and the cartridge housing and does not interact, directly or indirectly, with the outer shell 26. In addition, a proximal end of the needle cover 110 comprises a needle cover pin and this needle cover pin is configured to reside in a guide track provided along an outer surface of the rotator 60.

To initiate an injection with the drive mechanism of the delivery device 10, a user removes the cap 24 from the distal end 14 of the delivery device 10. After the cap 24 has been removed, the distally biased needle cover 110 is now free to initially move in a distal direction (arrow 140) by way of the needle cover spring 50 as illustrated in FIG. 11.

Figure 12:
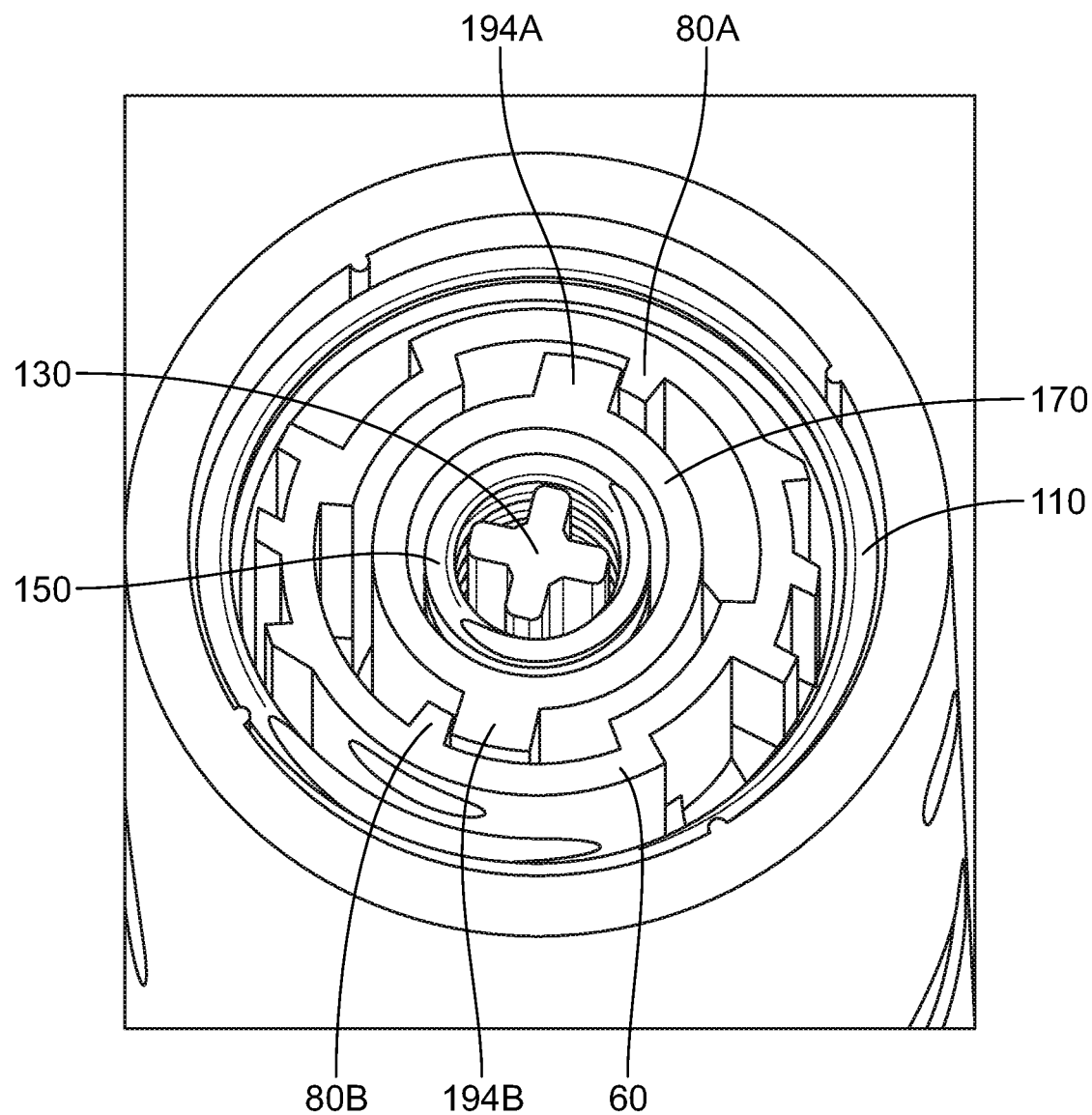
FIG. 12 is another diagrammatic representation of the drive mechanism illustrated in FIG. 11 with the cap removed.
Figure 13:
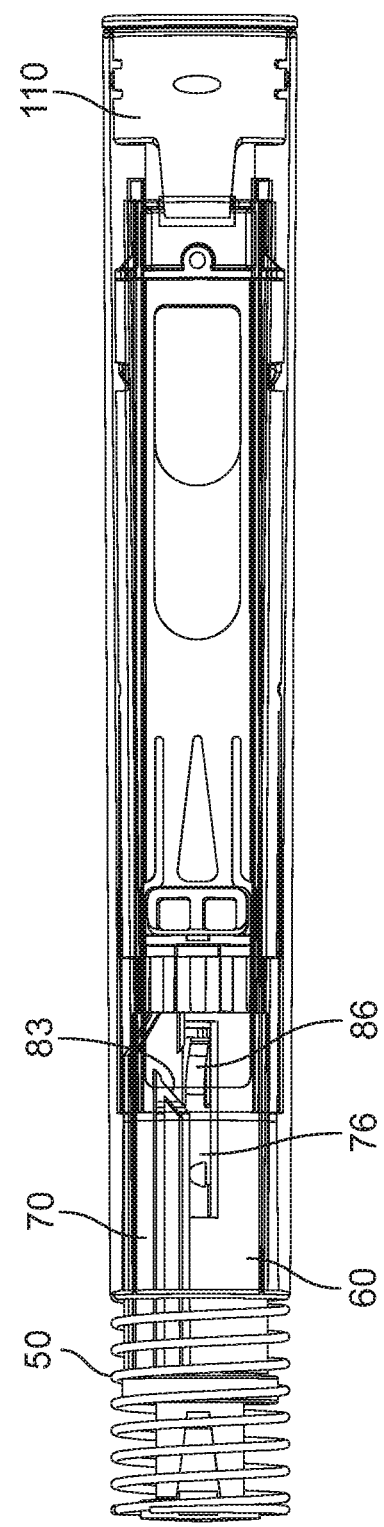
FIG. 13 is a diagrammatic representation of a proximal end of the drive mechanism illustrated in FIG. 10.
Figure 14:
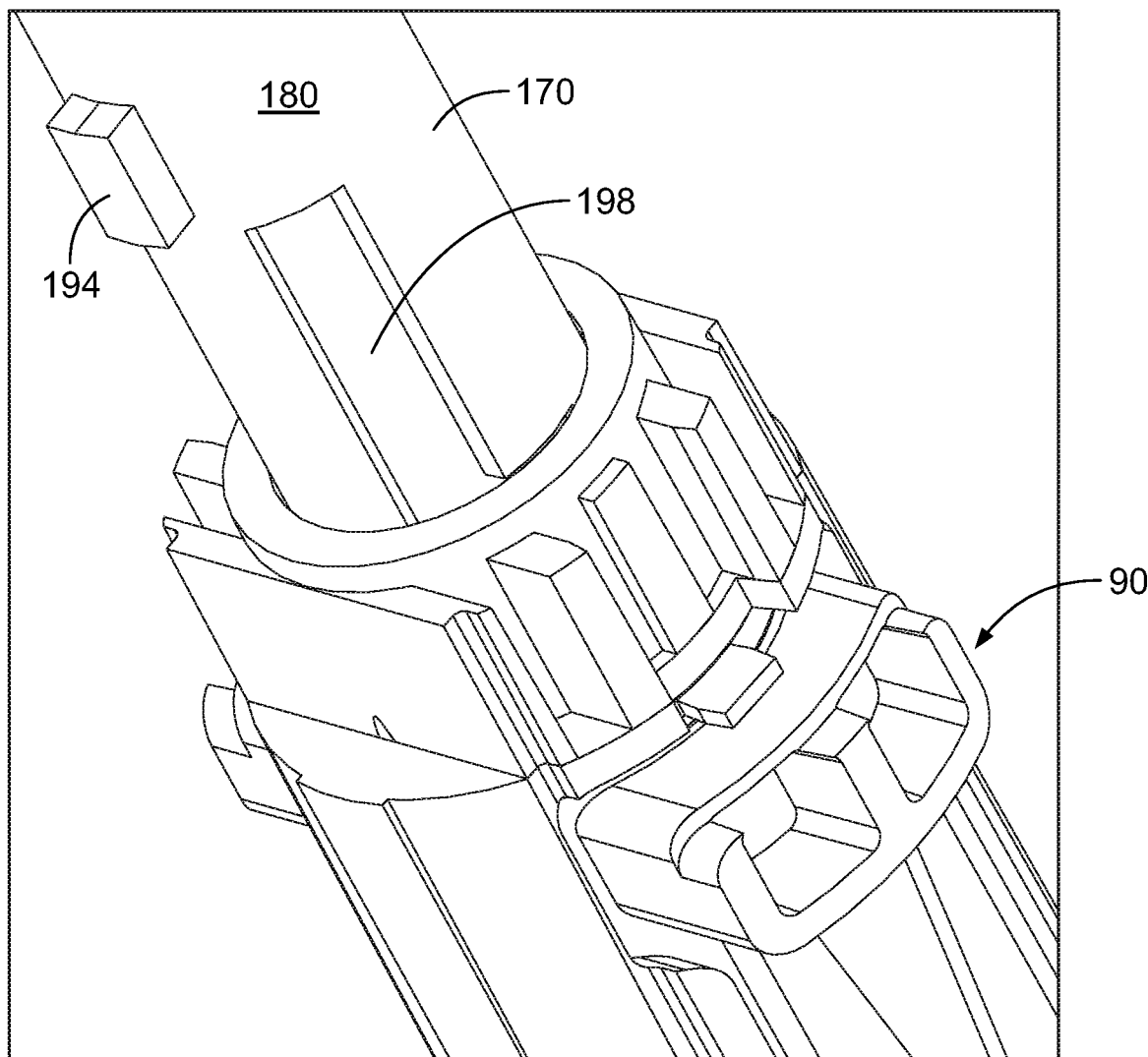
FIG. 14 is a diagrammatic representation of the drive mechanism illustrated in FIG. 11 during a proximal movement of a needle cover.

This initial distal movement of the needle cover 110, allows the needle cover pins 128 A, B residing on the needle cover 110 to move along the first track portion 72 defined along the outer surface 64 of the rotator 60. As the needle cover pins 128 A, B move along this first track portion 72 defined by the rotator 60 and the needle cover 110 is rotationally fixed to the outer shell 26, the needle cover pins 128 A, B impinge upon a first track wall 82 (FIGS. 6A, 6B, 11) causing an initial rotational movement of the rotator 60 relative to the plunger rod 170. This initial rotation of the rotator 60 aligns the inner ribs of the rotator with the 194 A, B of the plunger rod 170 as illustrated in FIG. 12. For example, the first inner rib 194A is now aligned with rotator rib 80 A and the second inner rib 194B is now aligned with the rotator rib 80 B. The needle cover pins 128 A, B will now reside in the second track portion 74 (FIGS. 6A and 6B).

To initiate an injection, the annular contact member 116 of the needle cover 110 is pressed against an injection site, wherein the needle penetrates the injection site and the injection is initiated. During this initial phase of the injection process, the needle cover 110 remains engaged with the rotator 60. As a distal end surface of the needle cover 110 is pressed against an injection site, the needle cover 110 will now move in a proximal direction.

This proximal movement of the needle cover 110 causes a further proximal movement of needle cover pins 128 A, B and they will now impinge upon a second track wall 83 (FIGS. 6A, 6B, 13) and then move along the third track portion 76 of the rotator 60. Impingement on the second track wall 83 causes a further rotational movement of the rotator 60.

This further rotational movement of the rotator 60 causes at least two things to occur. First, rotation of the rotator 60, and hence rotation of the inner ribs 80 A-D of the rotator 60, will act upon the outer ribs 194 A, B of the plunger rod 170, causing rotation of the plunger rod 170. Second, once the plunger rod 170 has been rotated by the internal ribs 80 A-D of the rotator 60, the plunger rod retention part 198 will be released from the ribs 102 A, B of the cartridge housing 90 will be free to move in the distal direction. (FIGS. 7A, 7B, 14) As such, the plunger spring 150 will now be released from its pre-tensioned state and force the now released plunger rod 170 to act on the stopper 214 contained within the cartridge 200, thereby initiating an injection.

Figure 15:
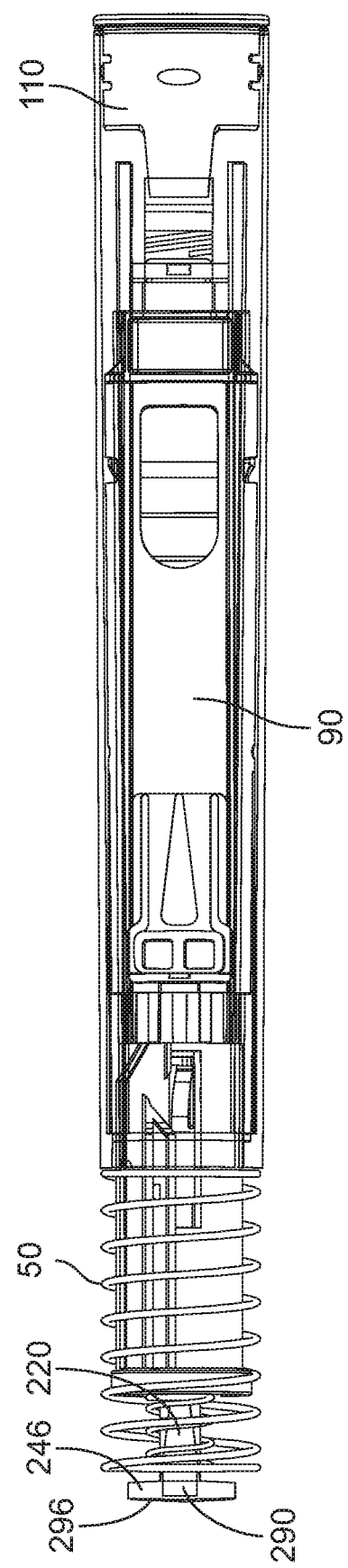
FIG. 15 is a diagrammatic representation of the proximal end of the drug delivery device illustrated in FIG. 9 after an injection.

After delivery, the delivery device 10 is removed from the injection site and the needle cover 110 will move back distally, driven by the needle cover spring 50. In this configuration, the needle cover pins 128 A, B will move in the distal direction along the third track portion 76 and over the locking arms 86 provided along the outer surface 64 of the rotator 60 (FIGS. 6A and 68). These locking arms 86 are biased radially, outwardly such that once the needle cover pins 128 A, B ride up over the locking arms 86, the needle cover pins 128 A, B will be prevented from any further proximal movement, thereby preventing re-use of the injection device 10 as illustrated in FIG. 15 (i.e., preventing any subsequent proximal movement of the needle cover 110 since the needle cover pins 128 AB cannot proximally surpass the radially outwardly directed locking arms 86).

Figure 16A:
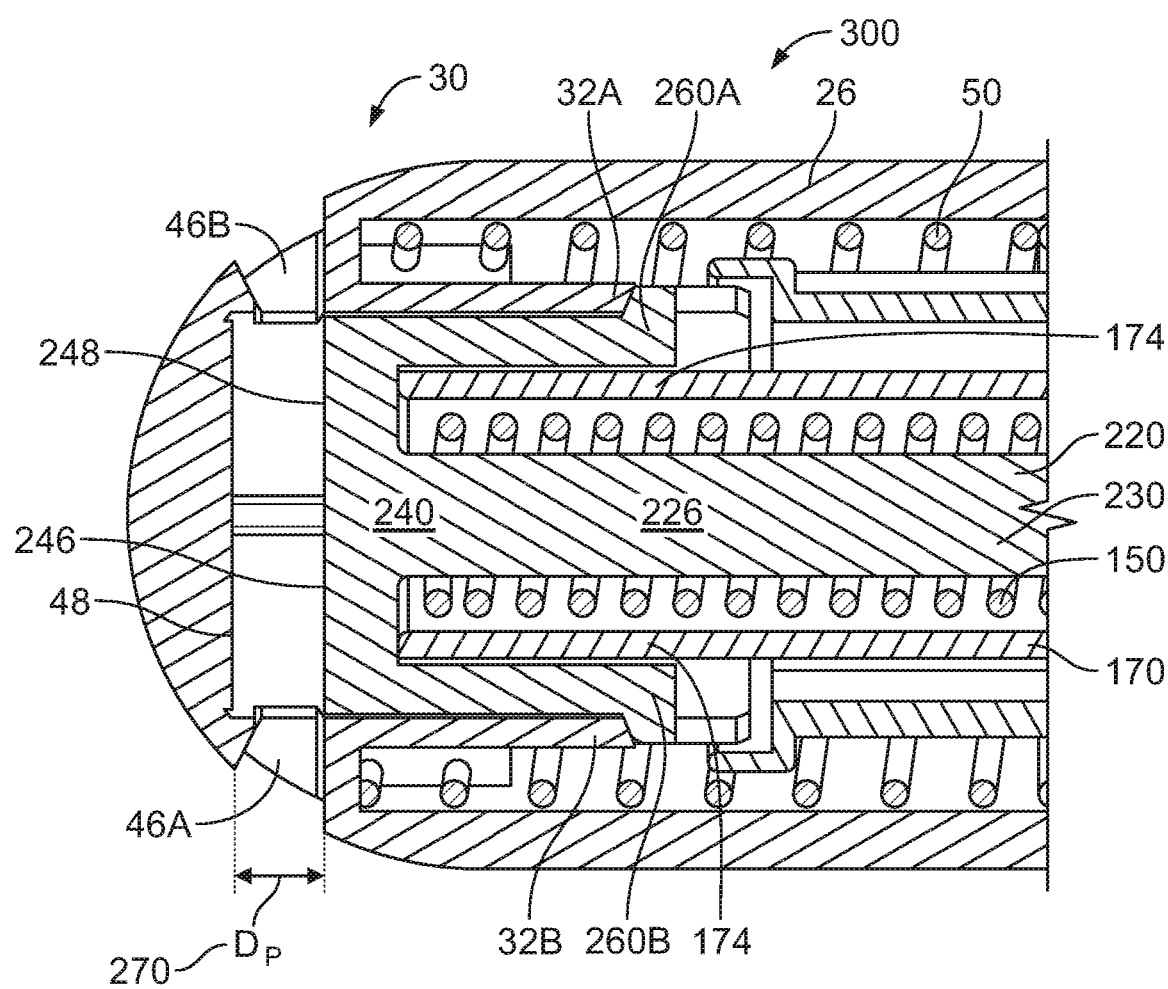
FIG. 16A is a diagrammatic representation of the proximal end of the drug delivery device illustrated in FIG. 9 before an injection.
Figure 16B:
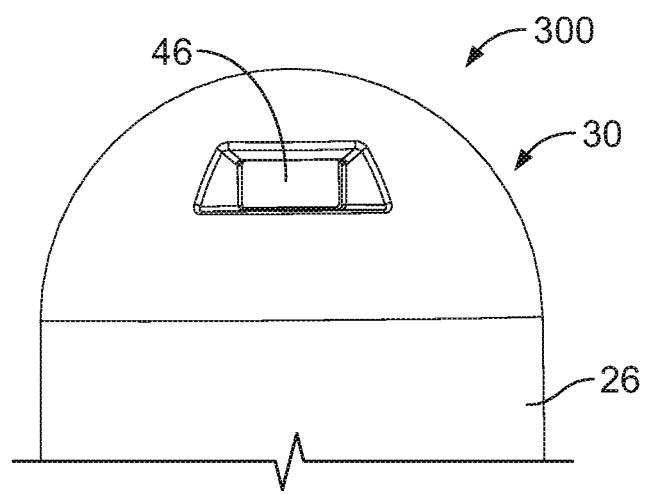
FIG. 16B is another diagrammatic representation of the proximal end of the drug delivery device illustrated in FIG. 9 before an injection.

As noted herein, the delivery device 10 further comprises an end of injection indication device 300 that operates to provide a signal (i.e., visual/tactile/audible) to a user when the injection has been completed. For example, FIG. 16A illustrates a diagrammatic representation of a proximal portion 20 of the delivery device 10 illustrated in FIG. 1 prior to an injection and illustrating a preferred arrangement of such an end of injection indication device 300. FIG. 16B illustrates another diagrammatic representation of a proximal portion 20 of the delivery device 10 illustrated in FIG. 1 prior to an injection. In one arrangement, such an indication device 300 may comprise the guide rod 220 (FIG. 8) that is releasably engaged to the delivery device, such as being hooked to the outer shell 26 of the delivery device 10. As just one example, the disk shaped member 240 of the guide rod 220 may be positioned a predetermined distance $D_P$ 270 away from the proximal end wall 48 of the outer shell 26 of the delivery device 10.

As illustrated and as discussed herein, the proximal end portion 20 of the delivery device 10 comprises a second viewing opening or window 46. In this illustration, two such viewing windows 46 A, B are provided. As illustrated, in the to be un-activated state before an injection occurs, the elongated stem portion 230 of the guide rod 220 resides within the plunger rod spring 150. Both the plunger rod spring 150 and the elongated member 230 of the guide rod 220 reside within the inner cavity 190 defined by the plunger rod 170. In this initial, pre-injection state, the chamfered edges 268 A, B of the outwardly directed hooks 266 A, B initially engage the outer shell retaining structures 32 A, B (FIGS. 3A and 38). As also previously discussed, the slots 254, 258 defined by the disk shaped member 240 slidably engage the guiding structures 36 of the outer shell 26 (FIGS. 3A, 38, and 8).

In FIGS. 16A and 16B, the flexible arms 260 A, B of the guide rod 220 are prevented from radially flexing inwardly (i.e., flexing towards each other) as the proximal end 174 of the plunger rod 170 acts as a stop so as to prevent these flexible arms 260 A, B from flexing inwardly, towards one another.

Figure 17A:
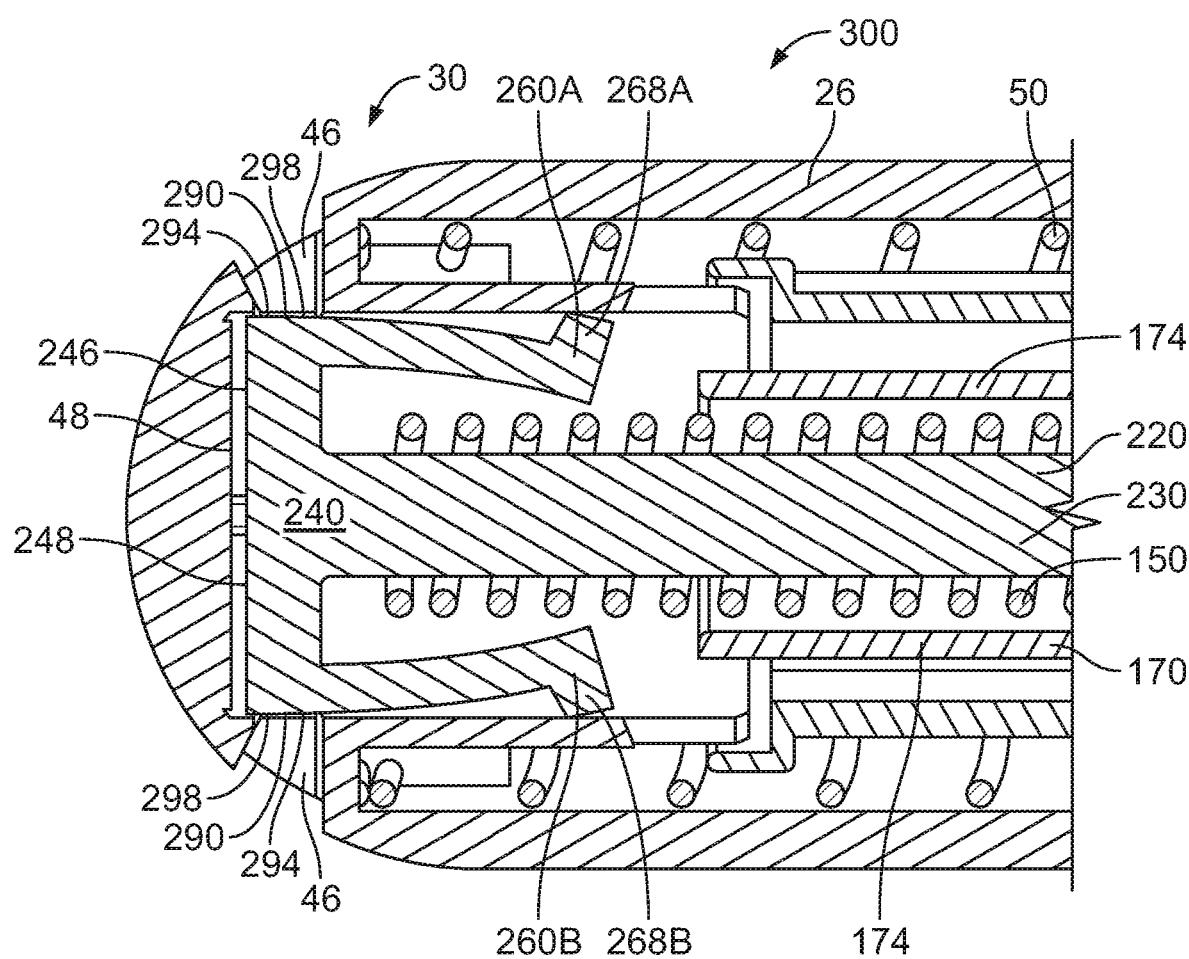
FIG. 17A is a diagrammatic representation of the proximal end of the drug delivery device illustrated in FIG. 16A after an injection.
Figure 17B:
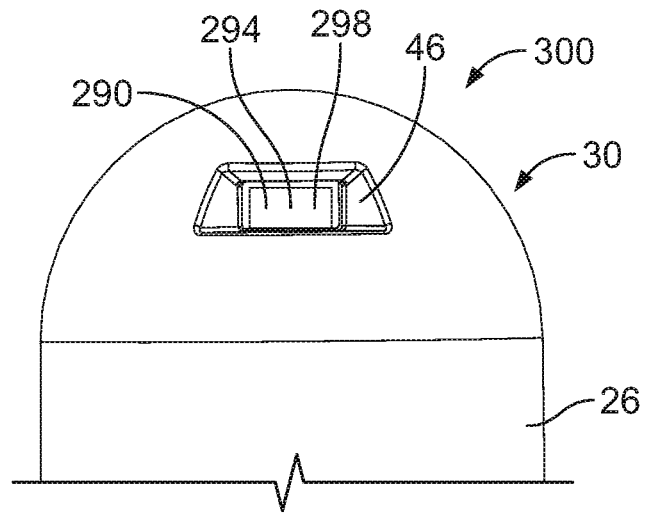
FIG. 17B is another diagrammatic representation of the proximal end of the drug delivery device illustrated in FIG. 16A after an injection.

FIG. 17A provides a diagrammatic representation of the proximal end portion 20 of the delivery device 10 illustrated in FIGS. 16 A and B after device activation. FIG. 17B provides another diagrammatic representation of the proximal portion 20 of the delivery device 10 illustrated in FIG. 1 prior to after device activation. As illustrated, in the activated state, the elongated stem portion 230 of the guide rod 220 still resides within the plunger rod spring 150 while both the plunger rod spring 150 and the elongated stem portion of the guide rod 220 reside within the inner cavity 190 defined by the plunger rod 170. The proximal bearing surface 248 of the disk shaped member 240 now resides along the back wall portion of the outer shell 26. In this preferred arrangement, the proximal bearing surface 248 comprises a flat surface.

At the end of the injection, the proximal portion 174 of the plunger rod 170 will move in the distal direction, thereby moving away from the flexible arms 260 A, B of the guide rod 220. In this manner, the flexible arms 260 A, B of the guide rod 220 are no longer prevented from radially flexing inwardly (i.e., flexing towards each other). As such, the flexible arms 260 A, B are now free to release the radially directed hooks 268 A, B from the retaining structures 32 A, B of the outer shell 26 and can now flex towards one another. Consequently, the guide rod 220 will now be released from the outer shell 26. As the guide rod 220 is now free to move, the guide rod 220 will be driven in the proximal direction by way of the plunger rod spring 150, towards the proximal end wall 48 of the outer shell 26. During this proximal movement, engagement of the guide rod slots 254, 258 with the outer shell guiding structures 32 A, B help guide or direct the guide rod 220 towards the proximal end wall 48. As the bearing surface 248 of the disk shaped member 240 contacts this proximal end wall 48, the impact of the bearing surface 248 on the proximal end wall 48 generates an audible and/or tactile signal or indication to the user of the delivery device 10, signaling completion of an injection step.

In addition, as the bearing surface 248 contacts this proximal end wall 48, as can be seen from FIG. 17B, the visual indicator 290 provided on the circular outwardly directed surface 280 of the disk shaped member 240 will now be seen by way of the viewing opening 46 of the outer shell 26. Again, engagement of the guide rod slots 254, 258 with the outer shell guiding structures 32 A, B help guide the guide rod 220 towards the proximal end wall 48 so that the visual indicator 290 may be properly aligned with the viewing windows 46 A, B. As mentioned herein, the visual indicator 290 may comprise text 294 and/or a label 298.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

We claim:

1. A drive mechanism for a delivery device, the drive mechanism comprising,
    a rotator comprising an outer surface and an inner surface, the rotator configured to rotate from a first position to a second position;
    a needle cover comprising an inner surface that engages the outer surface of the rotator;
    a plunger rod spring positioned within a cavity defined by the rotator;
    an end of injection indication device comprising a proximal end and a rod positioned at least partially within the plunger rod spring, where the end of injection indication device directly provides a signal to a user of the drive mechanism that an injection has been completed; and
    a rotatable plunger rod comprising an outer surface that directly engages with the inner surface of the rotator when the rotator moves from the first position to the second position causing the rotatable plunger rod to rotate with the rotator.

2. The drive mechanism of claim 1, wherein
    the rotator prevents axial movement of the rotatable plunger rod in a distal direction to thereby maintain the plunger rod spring in a pre-tensioned state exerting a force on the rotatable plunger rod.

3. The drive mechanism of claim 2, wherein preventing the axial movement of the rotatable plunger rod in the distal direction prevents proximal movement of the end of injection indication device.

4. The drive mechanism of claim 1 further comprising, at least one rib on the outer surface of the rotatable plunger rod.

5. The drive mechanism of claim 4, wherein at least one inner rib of the rotator is configured to releasably engage the at least one rib on the outer surface of the rotatable plunger rod.

6. The drive mechanism of claim 5,
wherein proximal movement of the needle cover moves the rotator from the first position to the second position, such that the at least one inner rib that projects radially inward from the inner surface of the rotator engages the at least one rib on the outer surface of the rotatable plunger rod thereby rotating the rotatable plunger rod.

7. The drive mechanism of claim 6, wherein
rotating the rotatable plunger rod enables axial movement of the rotatable plunger rod in a distal direction under a force created by the plunger rod spring.

8. The drive mechanism of claim 7, wherein
the axial movement of the rotatable plunger rod in the distal direction under the force created by the plunger rod spring allows proximal movement of the end of injection indication device under the force created by the plunger rod spring.

9. The drive mechanism of claim 8 wherein during the proximal movement of the end of injection indication device, a proximal bearing surface of the end of injection indication device impinges upon a proximal wall of the delivery device so as to create the signal to the user that the injection has been completed.

10. The drive mechanism of claim 9 wherein during the proximal movement of the end of injection indication device, the proximal bearing surface of the end of injection indication device impinges upon the proximal wall so as to create an audible signal to the user that the injection has been completed.

11. The drive mechanism of claim 9, wherein the end of injection indication device further provides a visual signal to the user that the injection has been completed.

12. The drive mechanism of claim 8, wherein during the proximal movement of the end of injection indication device, the end of injection indication device creates a visual signal to the user that the injection has been completed.

13. The drive mechanism of claim 1, wherein the end of injection indication device positioned within the plunger rod spring comprises:
a guide rod that extends from a distal end to the proximal end, the guide rod comprising: an elongated member extending from the distal end towards the proximal end; and
a disk shaped member provided near the proximal end of the elongated member.

14. The drive mechanism of claim 13,
wherein the disk shaped member further comprises:
a distal surface, and
a proximal surface, the proximal surface comprising a bearing surface configured for engaging a proximal end wall of the delivery device.

15. The drive mechanism of claim 14, wherein the distal surface of the disk shaped member further comprises a plurality of flexible arms, the plurality of flexible arms normally biased towards one another.

16. The drive mechanism of claim 15,
wherein the plurality of flexible arms extend in a distal direction.

17. The drive mechanism of claim 15,
wherein each of the plurality of flexible arms comprise a radially directed hook.

18. The drive mechanism of claim 17,
wherein each radially directed hook is configured to releasably engage a retaining structure defined by the delivery device.

19. The drive mechanism of claim 13,
wherein the disk shaped member further comprises at least one slot, the at least one slot configured to engage a guiding structure of the delivery device.

20. The drive mechanism of claim 1 further comprising a cartridge housing directly engaged with the rotatable plunger rod such that the rotatable plunger rod is prevented from moving proximally until the rotator moves from the first position to the second position causing the rotatable plunger rod to disengage from the cartridge housing.

21. A medicament delivery device comprising:
a drive mechanism comprising,
a rotator comprising an outer surface and an inner surface, the rotator configured to rotate from a first position to a second position;
a needle cover comprising an inner surface that engages the outer surface of the rotator;
a plunger rod spring positioned within a cavity defined by the rotator;
an end of injection indication device comprising a proximal end and a rod positioned at least partially within the plunger rod spring, where the end of injection indication device directly provides a signal to a user of the drive mechanism that an injection has been completed
a rotatable plunger rod comprising an outer surface that directly engages the inner surface of the rotator when the rotator moves from the first position to the second position causing the rotatable plunger rod to rotate with the rotator; and
an outer shell comprises a distal end and a proximal end and has a generally tubular shape, the outer shell further comprises a first viewing opening and a second viewing opening.

22. The medicament delivery device of claim 21, wherein the medicament delivery device resides in an initial non-activated state having a cap provided near a distal end of the medicament delivery device, where when the cap is manually operated and detached, the needle cover is moved by a force from a needle cover spring from a non-activated position to an activated position.

23. The medicament delivery device of claim 21, wherein the first viewing opening is provided near the distal end of the outer shell and the second viewing opening is provided near the proximal end of the outer shell, wherein a stopper in a medicament container is visible in the first viewing opening and the end of injection indication device is visible in the second viewing opening after the injection has been completed.

* * * * *